United States Patent [19]
Smith et al.

[11] Patent Number: 5,690,618
[45] Date of Patent: Nov. 25, 1997

[54] ELECTRONIC SYRINGE

[75] Inventors: Mark Timothy Smith, 375 St. James Street, London, Ontario, Canada, N6A 1X7; James William Ellis; Gerald Peter Keogh, both of London, Canada

[73] Assignee: Mark Timothy Smith, London, Canada

[21] Appl. No.: 392,225

[22] Filed: Feb. 22, 1995

[51] Int. Cl.$^6$ .................................................. A61M 5/00
[52] U.S. Cl. .......................... 604/232; 604/107; 604/207; 604/2; 120/DIG. 1
[58] Field of Search .................................. 604/187, 186, 604/207, 213, 232, 234, 30, 31, 65, 66, 67, 155, 235, 154; 128/DIG. 1

[56] References Cited

U.S. PATENT DOCUMENTS

| | | |
|---|---|---|
| 4,108,177 | 8/1978 | Pistor . |
| 4,525,164 | 6/1985 | Loeb et al. . |
| 4,617,016 | 10/1986 | Blomberg . |
| 4,634,431 | 1/1987 | Whitney et al. . |
| 4,662,872 | 5/1987 | Cané . |
| 4,668,220 | 5/1987 | Hawrylenko . |
| 4,719,825 | 1/1988 | LaHaye et al. . |
| 4,749,109 | 6/1988 | Kamen . |
| 4,781,700 | 11/1988 | Vicario . |
| 4,787,893 | 11/1988 | Villette . |
| 4,822,340 | 4/1989 | Kamstra . |
| 4,978,335 | 12/1990 | Arthur, III ........................ 604/67 |
| 5,102,393 | 4/1992 | Sarnoff et al. . |
| 5,269,762 | 12/1993 | Armbruster et al. . |
| 5,383,865 | 1/1995 | Michel ............................ 604/186 X |

FOREIGN PATENT DOCUMENTS

| | | |
|---|---|---|
| 0238398 | 9/1987 | European Pat. Off. . |
| 0246158 | 11/1987 | European Pat. Off. . |
| 0285679 | 10/1988 | European Pat. Off. . |
| 0293958 | 12/1988 | European Pat. Off. . |
| 0523343 | 1/1993 | European Pat. Off. . |
| 0595474 | 5/1994 | European Pat. Off. . |
| 2343486 | 10/1977 | France . |
| 3244791 | 7/1984 | Germany . |
| 8911310 | 11/1989 | WIPO . |
| 9302720 | 2/1993 | WIPO . |

*Primary Examiner*—Michael Powell Buiz
*Assistant Examiner*—N. Kent Gring
*Attorney, Agent, or Firm*—Fitzpatrick, Cella, Harper & Scinto

[57] ABSTRACT

An electronic syringe for use in administering anesthetic and the like injections or for aspirating fluids. The electronic syringe is particularly well suited in dental applications where a precise level of hand control is required. The syringe housing is a compact, pen-style arrangement that may be gripped between the middle and index fingers of the practitioner's hand which allowing for thumb-free operation. Motorized, optionally cordless, operation with speed control and data collection is also provided such that an injection can be preformed on a patient in a steady, painless, non-intimidating manner. When connected to a processing device, the data collection feature is capable of updating a patient database with the mount of anesthetic and the like injected for record keeping purposes.

31 Claims, 4 Drawing Sheets

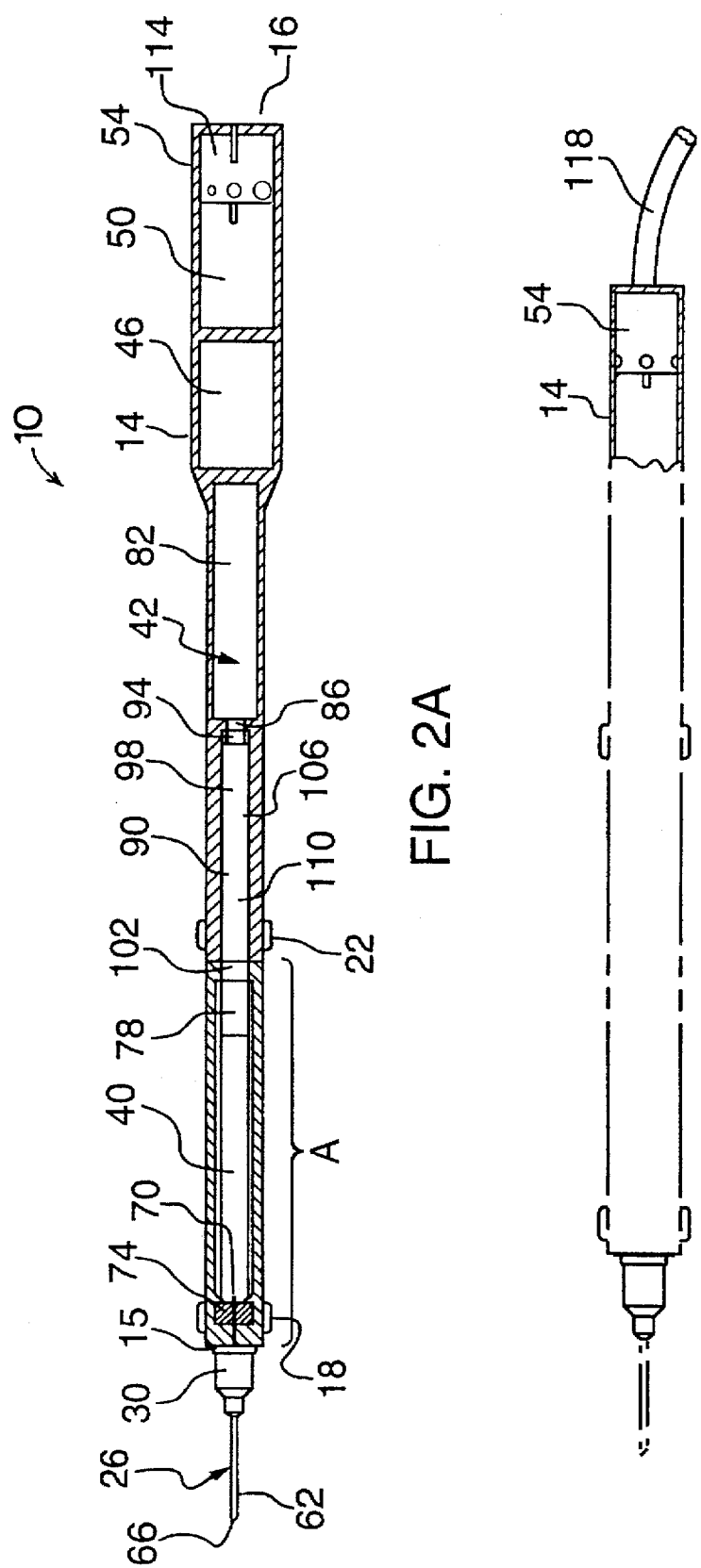

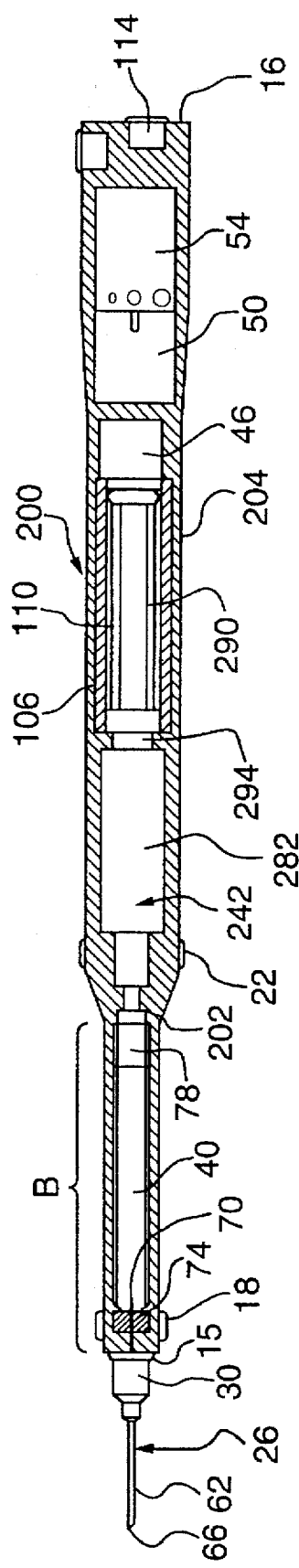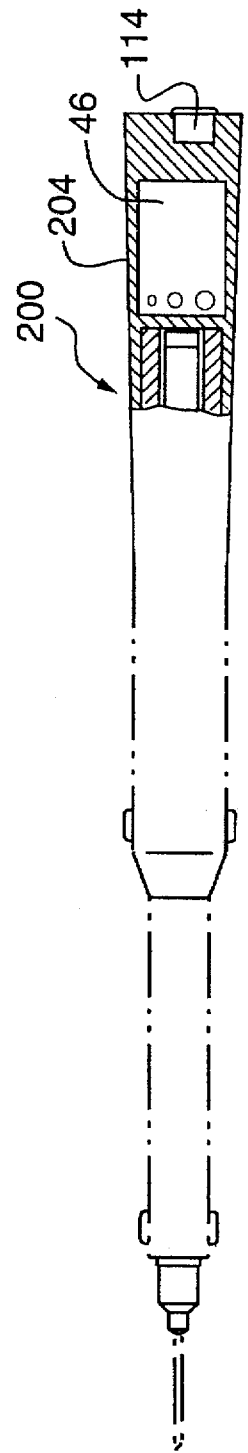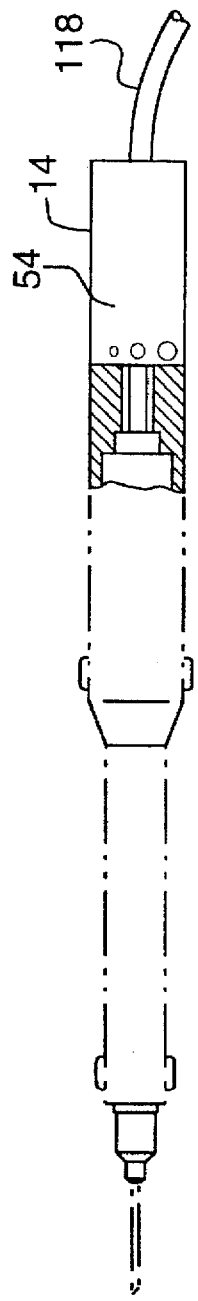
FIG. 3A
FIG. 3B
FIG. 3C

ELECTRONIC SYRINGE

BACKGROUND OF THE INVENTION

1. Field of the Invention

The present invention relates to an electronic syringe, and more particularly to a compact, pen-style grip, electronic syringe that allows a practitioner to administer injections or aspirations at a controlled rate and with a precise degree of hand control thereby minimizing or eliminating patient fear and discomfort.

2. Description of the Prior Art

Electronic syringes are known in the art. Typical uses for such devices include injecting biocompatible material, specifically anaesthetic such as block, conduction and paraapical anaesthesia, through bone tissue and administering insulin and other pharmaceuticals.

In most dental applications, practitioners are required to regularly administer anaesthetic injections in confined spaces using conventional manual syringes.

Conventional manual syringes, as used in dentistry applications, usually comprise a hollow cylindrical housing having one end adapted to receive a needle and the other end adapted to receive a piston assembly. The outer surface of the housing is provided with a pair of finger grips such that the device can be held firmly between the middle and index fingers of the practitioner's hand. Anaesthetic is commonly supplied in premeasured ampoules which are designed to fit into the housing. The ampoule has one end provided with a pierceable membrane that receives the needle in sealing engagement and another end fitted with a slidable plunger which engages the piston assembly. The piston assembly includes a shaft, one end of which is fitted with a plunger, and an opposing end provided with a thumbrest. In operation, the anaesthetic injection is administered by depressing the plunger with the practitioner's thumb which causes the piston to engage the plunger, thereby forcing anaesthetic from the ampoule via the needle.

There are several disadvantages associated with conventional manual syringes used in dentistry applications. For example, due to uneven thumb pressure applied on the thumbrest, the practitioner has very little control over the flow rate of anaesthetic exiting the needle. As a result it is virtually impossible to achieve a substantially constant flow rate with a manual syringe. Further, many practitioners often complain that, due to the manner by which a conventional manual syringe is grasped, such a syringe offers poor control of the needle tip when administering the injection. As a result, unsteady injections cause unnecessary pain and discomfort to the patient. Still further, it is generally uncontested that the majority of patients dislike the thought of receiving an injection, especially a dental injection. Indeed, this aversion is usually due to the fact that many manual syringes are highly intimidating in appearance.

The prior art has attempted to address various of these disadvantages, with little or no success.

U.S. Pat. No. 4,617,016 (Blomberg) teaches an insulin injection device adapted to accommodate conventional disposable syringes. Through the use of a motor in communication with a transmission and lead screw, the device that is capable of being used to load an empty syringe with a predetermined amount of insulin from an external ampoule prior to injecting. Unfortunately, the device is cumbersome and somewhat intimidating to the patient. Another disadvantage is that using a conventional hypodermic syringe, which must be replaced between injections, adds to the operating cost of the unit. Yet another disadvantage is that there is no means for tracking the amount of insulin injected.

U.S. Pat. No. 5,269,762 (Armbruster et al.) teaches a portable hand-held power assister device for injecting a liquid, such as X-ray contrast media, into the vascular system of a mammal at a single constant rate. The assister device is a pistol type arrangement that externally receives a conventional syringe onto the front of the unit. A connector, coupled to one end of a lead screw/transmission drive engages the thumbrest on the syringe. A forward-reverse switch is provided which is used to load and dispense the syringe. Clearly, this device is not suited for finely controlled variable rate injections (e.g. for dental applications) and is intended to be used remotely of the patient via a butterfly needle. Thus, in a dental application (and other applications), the device cannot provide the delicate and precise hand control necessary to administer an injection without the patient experiencing discomfort.

It would be desirable to have an electronic device capable of dispensing a fluid at a constant and precise rate. It would also be advantageous if such a device could be operated in a "thumb-less" manner and was configured to allow the practitioner to have precise control of the amount of fluid being administered. It would also be further advantageous if the device was configured to be less intimidating than the prior art devices.

SUMMARY OF THE INVENTION

It is an objective of the present invention to provide an electronic syringe which obviates or mitigates at least one of the above-mentioned disadvantages of the prior art.

Accordingly, in one of its aspects, the present invention provides an electronic syringe comprising:

a generally elongate housing comprising a needle and electronic control means at opposite ends thereof;

an ampoule receiving first portion disposed in the housing adjacent the needle;

drive means in electrical communication with the electronic control means;

a plunger disposed between the first portion and the drive means, the drive means actuating the plunger through the first portion; and switch means located on the housing for actuating the drive means.

Thus, the present invention relates to an electronic syringe. As used throughout this specification the term "electronic syringe" has a broad meaning and is intended to encompass a device used for injection or aspiration, as warranted by the intended application.

Further, as used throughout this specification, the term "electronic", when used in the context of describing an injection syringe, is intended to have a broad meaning which encompasses an injection syringe wherein at least a portion of the energy requirement to actuate the plunger in the syringe is achieved electrically.

BRIEF DESCRIPTION OF THE DRAWINGS

Embodiments of the present invention will be described with reference to the accompanying drawings, in which:

FIG. 2a illustrates a sectional view of a syringe similar to the one illustrated in FIG. 1 and adapted to include a battery power supply;

FIG. 2b illustrates a sectional view of a syringe similar to the one illustrated in FIG. 1 and adapted to include an umbilical cord;

FIG. 3a illustrates a sectional view of an electronic syringe in accordance with another embodiment of the present invention and adapted to include a battery power supply;

FIG. 3b illustrates a sectional view of a syringe similar to the one illustrated in FIG. 3a and adapted to include a battery power supply;

FIG. 3c illustrates a sectional view of a syringe similar to the one illustrated in FIG. 3a and adapted to include an umbilical cord.

In the Figures, like reference numerals are used to designate like elements.

DETAILED DESCRIPTION OF THE PREFERRED EMBODIMENTS

Figure 1:
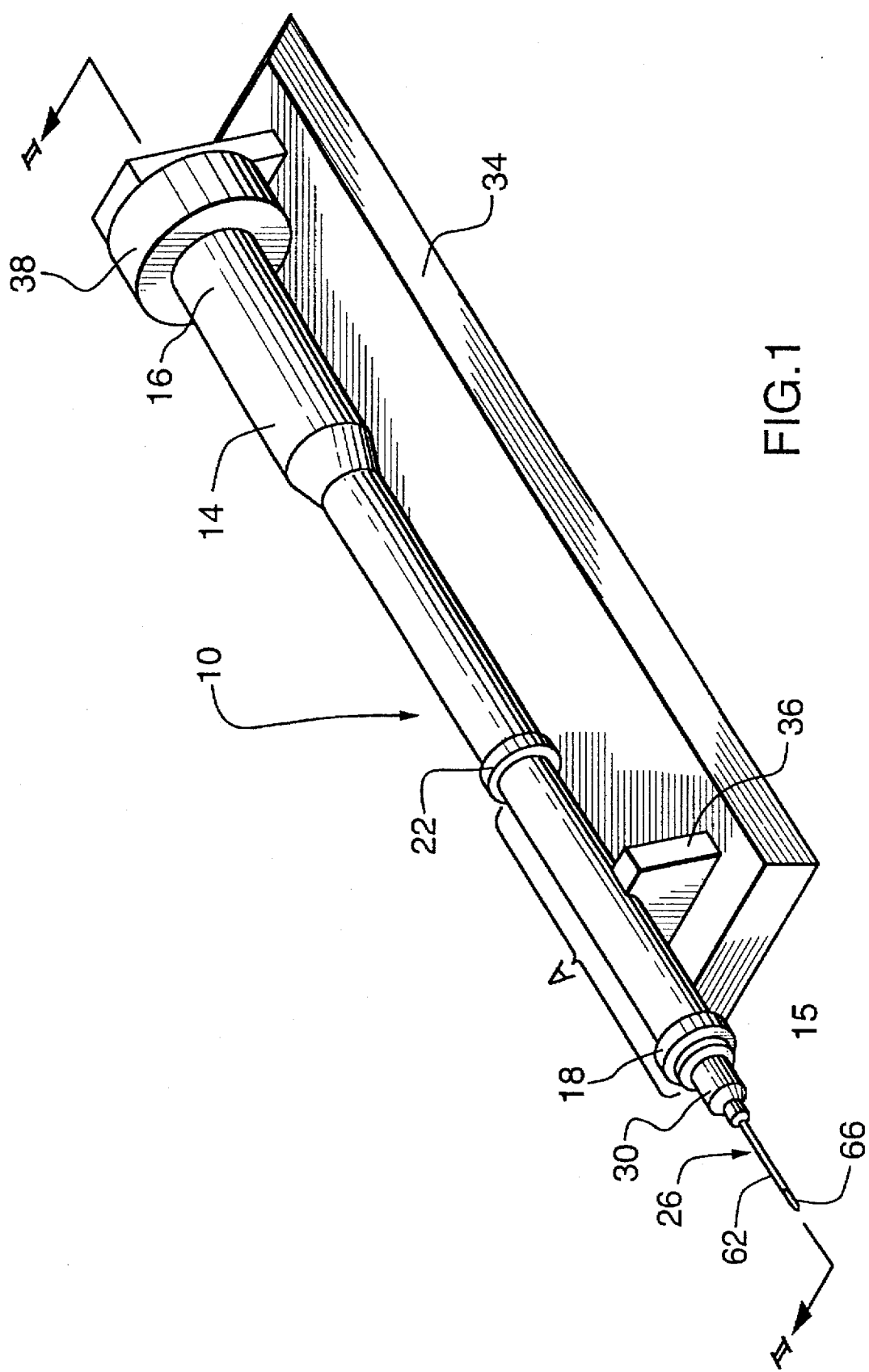
FIG. 1 illustrates a perspective view of an electronic syringe in accordance with an embodiment of the present invention.

With reference to FIG. 1 there is illustrated an electronic syringe 10 in accordance with an embodiment of the present invention. As can be seen in the Figure, syringe 10 includes a elongate housing 14 of varying circular cross-section, having a pair of ends 15,16 and control switches 18,22. A needle 26 is provided with a collar 30 and is removably received by end 15. Housing 14 assumes the appearance and feel similar to that of a pen which provides the practitioner with an enhanced comfort level, thereby providing confident, steady and a precise degree of hand control. To the patient, the pen-like appearance is much less intimidating when compared to conventional electronic syringe devices.

Housing 14 is preferably moulded from a medical grade plastic material such as a liquid crystal polymer commercially available from Hoechst Celanese under the tradename Vectra LCP™. Another possible alternate material is medical grade Lexan™ commercially available from General Electric Plastics. The type of material used to mould the housing would depend on the exact method of sterilization to be used and the type of application in which syringe 10 will be subjected or the environment in which it will be used.

A base member 34 includes a cradle 36 and an interface socket 38. Base member 34 is used to store and recharge syringe 10 when not in use and is also used to collect data via socket 38 when syringe 10 is placed in the base. The operation of collecting data and recharging syringe 10 will be described in greater detail hereinafter.

Needle 26 comprises a collar 30 through which is passed a hollow shaft 62. Shaft 62 acts as a passageway for fluid passing between a tip 66 in needle 26, adapted for piercing tissue, and an inward end 70 adapted for piercing an ampoule containing a fluid. Needle 26 is typically available in three common sizes, namely 25, 27 and 30 gauge. The gauge sizes correspond to the outside diameter of hollow shaft 62.

As shown in FIG. 2a, the internals of syringe 10 comprise a removable ampoule 40, a drive system 42, an electronic control system 46, a battery 50 and a fluid rate switch 54.

Ampoule 40 is a conventional, generally cylindrical, disposable container used to package prepared fluids such as medicants, anaesthetics and the like. Ampoule 40 is provided with a pair of ends, one end having a pierceable membrane 74 which receives inward end 70 of needle 26 in sealing engagement. The opposing end of ampoule 40 is fitted with an internally slidable plunger 78.

Switches 18,22 are clamshell, on/off, finger pressure sensitive switches that encircle housing 14 and are used to stop and start the operation of syringe 10. The use of this type of switch enables operation of syringe 10 through 360° about the longitudinal axis of the unit without having to rotate the device to access either of switches 18,22. Switch 18 is mounted in close proximity to end 15 to facilitate injections requiring the practitioner's hand to be positioned near needle 26 for freer control. Switch 22 is mounted towards the middle of housing 14 and provides operating control when the practitioner requires a longer reach. Fluid rate switch 54 is a rotary, three position selector which allows the practitioner to select from three speed settings namely, slow, medium and fast and are selected depending on the size of needle 26 selected.

Battery 50 is preferably a conventional rechargeable AA type unit. External connections to a conventional battery charger power supply (not shown) and the data communication circuit (not shown) are accomplished via metal contact strips 114 moulded into end 16 of housing 14. Contact strips 114 mate with complementary contact strips provided in socket 38 of base member 34.

Drive system 42 comprises a lead screw 90, a lead nut 94, a motor 82, a thin walled tube 98 and a piston 102. Lead screw 90 has a proximal end directly coupled to the shaft of motor 82, and a free distal end. Lead nut 94 engages lead screw 90 in a complementary manner and is movable along lead screw 90 between a fully retracted and a fully extended position. Tube 98 freely surrounds lead screw 90 and has one end fixedly attached to lead nut 94. The opposing end of tube 98 is fitted to piston 102 and is long enough such that piston 102 does not interfere with the distal end of lead screw 90 when lead nut 94 is in the fully retracted position. As shown in FIG. 2a, the fully retracted position is such that lead nut 94 is near the proximal end of lead screw 90 and piston 102 is in close coupling proximity with plunger 78 when ampoule 40 is full. The fully retracted position is the normal resting position when syringe 10 is not in use. In the fully extended position, the proximal end of lead screw 90 is near lead nut 94. It is preferred that lead screw 90 has a stroke length such that, at the fully extended position, piston 102 and plunger 78 have translated to fully dispense the contents of ampoule 40.

The engagement of lead nut 94 with lead screw 90 is such that there exists a small amount of backlash or "play" to allow for momentary "self aspiration" caused by back pressure in the tissue when first pierced by needle 26. Typically, upon piercing, a small amount of blood will enter ampoule 40 as the back pressure in the tissue equalizes that in ampoule 40. As the pressure equalizes, a force is transmitted to lead screw 90 via lead nut 94 as plunger 78 presses against piston 102. A certain amount of backlash is required to absorb the force created by pressure equalization. This self aspiration assists the practitioner in determining whether a blood vessel has been pierced. As would be apparent to one of skill in the art, other methods of introducing "play" into drive system 42 exist. For example, "play" may be introduced into drive system 42 by employing a flexible coupling, spring or having plunger 78 and piston 102 sit in a spaced relationship initially upon insertion of ampoule 40 into syringe 10.

Preferably, motor 82 is a Series 1016, miniature DC motor manufactured by MicroMo Electronics Inc. and includes a 64:1 10/1 gearhead and a Series HE encoder (not shown).

Lead screw 90 is a conventional stainless steel lead screw as that manufactured by Kerk Motion Products Inc. and may include a Teflon™ coating which serves to extend the life thereof. Lead nut 94 is a conventional off-the-shelf component also manufactured by Kerk Motion Products Inc. and is preferably formed from Acetal™ which is a self-lubricating plastic having long life characteristics. As is known in the art, Acetal™ is commercially available E.I. Du Pont de Nemours and Company.

A feedback sensor 106 which comprises a high resolution potentiometer strip 110 mounted to the outer surface of tube 98. A wiper contact (not shown), fixedly attached to the inner surface of housing 14, contacts potentiometer strip 110 as lead nut 94 moves tube 98 along lead screw 90. The motion of potentiometer strip 110 along the wiper contact which causes a variation in electrical resistance through potentiometer strip 110 which is converted into positional information by electronic control system 46. A non-limiting example of a suitable feedback sensor 106 is manufactured by Data Instruments Inc. and is commercially available under model name MystR™.

Figure 4:
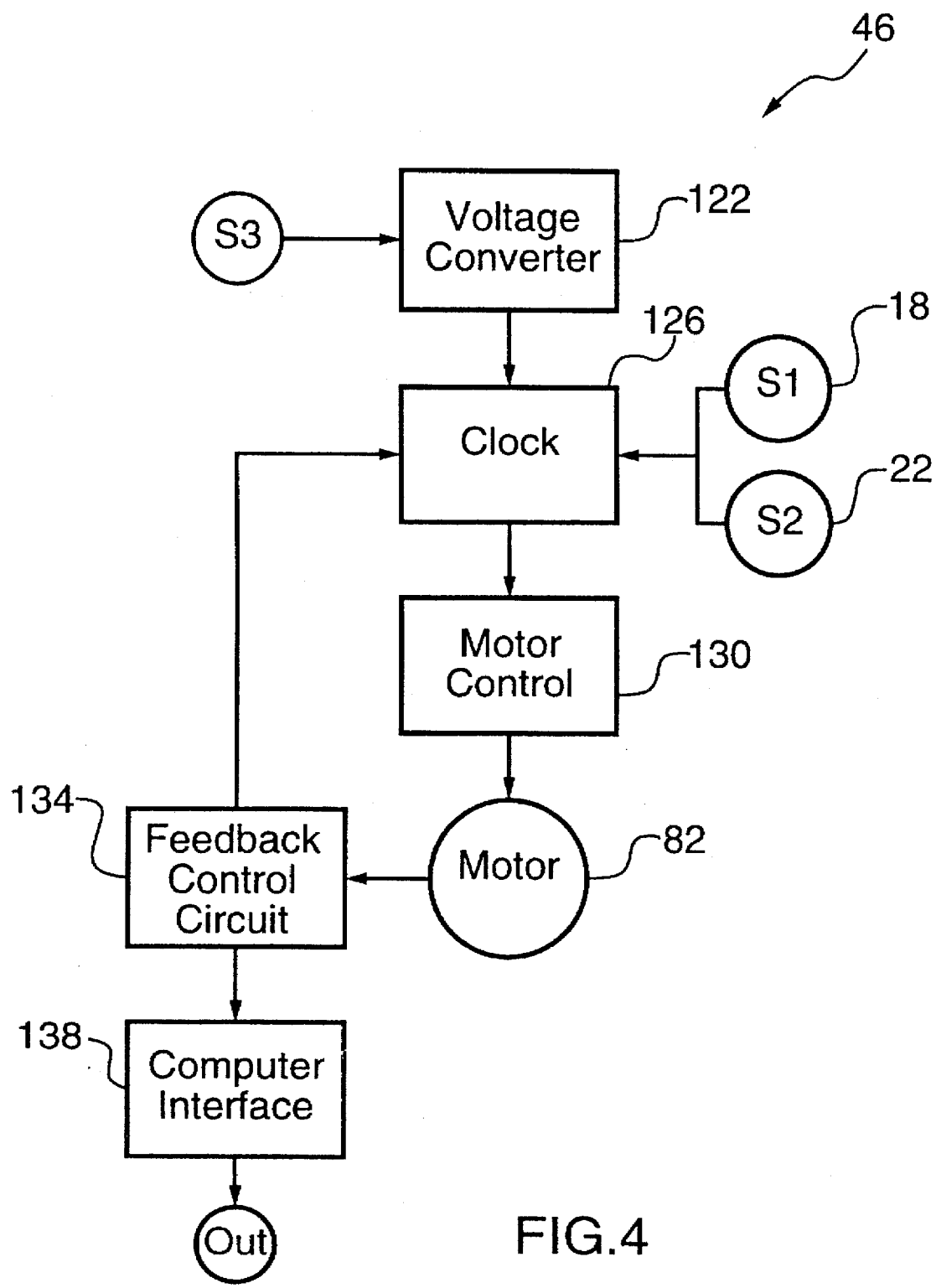
FIG. 4 illustrates a block diagram of an electronic control circuit in accordance with an embodiment of the present invention.

With reference to FIG. 4, electronic control system 46 comprises a battery charge interface (not shown), a voltage converter 122, a counter 126, a motor control circuit 130, a feedback control circuit 134 and a computer interface 138. Fluid rate switch 54 determines the desired flow rate by providing voltage converter 122 with an input voltage proportional to the desired flow rate. This causes voltage converter 122 to output a frequency pulse proportional to injection flow rate. The frequency output pulse from voltage converter 122 is input to counter 126 which counts one incremental step for each input pulse from a predetermined maximum value, representing a full ampoule, to zero, representing an empty ampoule. Each incremental step of the counter is passed to a high current driver portion of the motor control circuit 130 which rotates motor 82 in microstep increments. In this regard, the feedback control circuit, connected to feedback sensor 106, provides a precise voltage that is directly proportional to the position of piston 102 and the volume amount of injected material.

Computer interface 138 enables syringe 10 to maintain a record of the amount of anaesthetic administered during an operating cycle. Feedback control circuit 134 provides the proportional voltage that is scaled and held by computer interface 138 until syringe 10 is placed in base 34. As would be apparent to one of skill in the art, base member 34 further includes components of electronic control system 46, sufficient to facilitate communication with a processing device. Specifically, the communication circuitry comprises a analog to digital converter, memory, a microcontroller, a conventional asynchronous serial communication means and complementary electrical contacts disposed in socket 38. The processing device can be any one of a number of devices including IBM™ and compatible personal computers, Apple™ Computers, RISC based systems, or larger type systems and the like.

When syringe 10 is placed in base 34, the microcontroller senses a voltage at the complementary electrical contacts and activates the communication circuitry. The stored voltage representing volume information is passed to the analog to digital converter where the signal is converted into a digital volume representation and stored in the memory unit. The digital value is then transmitted to the processing device via a suitable communication means such as a RS232 asynchronous communication adaptor and the like, such that patient databases may be updated.

In the event that data collection and record updating is not a requirement for the specific application, the data collection circuitry can be eliminated from syringe 10 which will result in a smaller, more compact housing. Components required for data transmission, disposed in base member 34, will also be eliminated.

As illustrated in FIG. 2b, it is possible to replace electronic control system 46 and battery 50 with a power/data umbilical cable 118. Eliminating these components from syringe 10 allows for a smaller more compact housing 14. In many applications, a more compact model may be desired over the cordless, but bulkier, feature of syringe 10. The previously mentioned battery charger components would be replaced with a conventional DC power supply in electronic control system 46 and housed in base member 34.

In development of the present electronic syringe, it has been determined that patients suffer the most discomfort when injection fluid enters the tissue. The patient will also experience pain if the flow rate of anaesthetic entering the tissue is too fast. It has been determined that typical injections take from 15 seconds to 45 seconds to administer approximately 1.8 ml of anaesthetic depending on the size of needle diameter employed. As discussed above, dental practitioners typically employ three sizes of needle, namely: 25, 27 and 30 gauge. In order to facilitate an anaesthetic injection with minimal discomfort to the patient, flow properties of a typical anaesthetic injection should be as expressed in Table 1.

TABLE 1

| Dispensing Time (sec) | Needle Gauge | Flow Rate (mL/s) | Needle Exit Velocity (cm/s) | Ampoule Fluid Velocity (cm/s) |
|---|---|---|---|---|
| 45 | 30 | 0.04 | 200 | 0.113 |
| 30 | 27 | 0.06 | 175 | 0.170 |
| 15 | 25 | 0.12 | 225 | 0.340 |

It has also been determined that, based on the smallest needle diameter (30 gauge), the maximum constant force required to successfully administer the anaesthetic injection, without having the patient experience discomfort, is approximately 1.5 lbs.

With this in mind, the operation of administering an injection, in accordance with the present invention, will now be described with reference to FIG. 2a. Ampoule 40 is pushed into housing 14 via end 15 until fully seated in the position shown in the Figure. Needle 26 is then placed into end 15 forcing inward end 70 to pierce membrane 74 in sealing engagement with ampoule 40. Fluid rate switch 54 is then used to select the desired injection rate as determined by the selected size of needle 26 and as indicated in Table 1. Syringe 10 is gripped between the thumb and index finger of the practitioner's hand in a manner similar to that of holding a pen or pencil as previously described. The practitioner's index finger extends to activate either of switches 18,22. Providing syringe 10 with a pen style housing 14 enables the practitioner to exercise superior hand control and provide steady injections while substantially decreasing patient discomfort. The pen style housing is also substantially less intimidating to the patient and allows for thumb-free operation of the device.

Lead nut 94, coupled to tube 98 and piston 102 is in the fully retracted position. When switch 18 (or 22) is depressed, electronic control system 46 activates motor 82 effecting rotation of lead screw 90 which advances lead nut 94, tube 98 and piston 102 in the forward direction. Piston 102 couples with plunger 78 and forces the plunger through ampoule 40 dispensing fluid through hollow shaft 62, out tip 66 thereby accomplishing the injection. When switch 18 is released, motor 82 stops and the injection is halted. Once switch 18 or 22 is depressed again, operation resumes and the injection continues.

Electrically, electronic control system 46 operates motor 82 in the following manner. When the practitioner activates either of switches 18 or 22, voltage converter 122 is activated and outputs pulses at a frequency proportional to the injection rate as selected by fluid rate switch. As previously mentioned, the output pulses pass counter 126 and through motor control circuit 130 effecting motor 82 to advance in micro-step increments. Each micro-step corresponds to a specific amount of fluid volume dispensed. In order to track the amount of fluid dispensed, the counter counts pulses down from a maximum value, corresponding to a full ampoule 40, to zero, corresponding to an empty ampoule 40. Feedback sensor 106 via feedback control circuit 134 provides a voltage which is proportional to the mount of volume dispensed and is stored in computer interface 138 until syringe 10 is returned to base 34.

Once the timer has reached zero, and a check with the volume dispensed as determined by feedback sensor 106 indicates that ampoule 40 is empty, by lead nut 94 being in the fully extended position, motor 82 is automatically reversed. The reversing motion translates lead nut 94, tube 98 and piston 102 back to the fully retracted position. Once feedback sensor 106 indicates the fully retracted position has been reached, motor 82 is turned off and the operation cycle is complete. At this point needle assembly 26 and ampoule 40 may be removed from the unit and discarded.

When the unit has been returned to base member 34, data representing the amount of anaesthetic injected is transmitted via contact strips 114 and socket 38 to the processing device operating the patient database. By retrieving this information from syringe 10, an accurate patient record can be obtained by providing automatic updating. Once the data has been retrieved from electronic control means 46, the memory is cleared and syringe 10 is reset and ready for another operating cycle.

An alternative embodiment in accordance with the present invention is shown in FIGS. 3a, 3b, and 3c and, in these Figures, like elements to those of the above described embodiment of FIGS. 1, 2a and 2b are indicated with like reference numerals.

Thus, with reference to FIG. 3a, an electronic syringe 200 is provided with an elongate housing 204 of varying circular cross-section. In this embodiment, a drive system is used which differs from the one employed in FIGS. 1, 2a and 2b. A drive system 242 comprises a combination lead screw 290 and a motor 282, a piston 202 and lead nut 294. Lead nut 294 is fixedly attached with the rotor of motor 282, which, as it rotates, drives lead screw 290 axially through motor 282. Combined lead screw 290 and motor 282 may be obtained from Haydon Switch and Instrument Inc.

Lead screw 290 has a free proximal end, which allows axial translation between a fully retracted and a fully extended position, and a distal end directly coupled to piston 202. As shown in the Figures, the fully retracted position is such that the proximal end of lead screw 290 is fully retracted into housing 204 and piston 202 is in dose proximity with plunger 78 when ampoule 40 is full. Again, the fully retracted position is the normal resting position when syringe 10 is not in use. The fully extended position is such that the proximal end of lead screw 90 is near lead nut 294. It is preferred that lead screw 290 has a stroke length such that, at the fully extended position, piston 102 and plunger 78 have translated to fully dispense the contents of ampoule 40.

Drive system 242 further includes feedback sensor 106 having high resolution potentiometer strip 110 mounted to the inner surface of housing 204, along the length of the stroke of lead screw 290. The wiper contact (not shown), fixedly attached to the proximal end of lead screw 290, contacts potentiometer strip 110 as the lead screw translates through motor 282 and lead nut 294. The function of feedback sensor 110 is substantially identical as that previously described.

As shown in FIG. 3b, in the event that data collection and record updating is not a requirement for the specific application, the data collection circuitry can be eliminated from syringe 200 which will result in a smaller, more compact housing. Components required for data transmission, disposed in base member 34, will also be eliminated.

As shown in FIG. 3c, and similar to FIG. 2b, it is contemplated that electronic control system 46 and battery 50 may be replaced with a power/data umbilical cable 118. Eliminating these components from syringe 200 allows for a smaller more compact housing 204. In many applications, a more compact model may be desired over the cordless, yet bulkier, feature of syringe 200. The previously mentioned battery charger components would be replaced with a conventional DC power supply in electronic control system 46 and housed in base member 34.

Functionally, the operation of syringe 200 is substantially the same as that of the previously-described embodiment. Mechanically, the major operating difference with respect to the previously-described embodiment is that lead screw 290 translates through motor 282 and lead nut 294 eliminating the requirement of the previously described tube 98.

It is contemplated that communications between syringe 10 and the processing device may be further enhanced by provided the ability to load data to syringe 10 in addition to presently transferring data from the syringe. For example, a practitioner using a personal (or other) computer and preparing to administer an injection, would retrieve the patient record from the patient database. The practitioner then selects from a menu, or enters directly, the type of anaesthetic about to be administered. The computer could verify, based on information available, whether the patient is sensitive to the anaesthetic selected and offer alternatives. Should the patient record indicate any other special requirements for example, patient history with respect to pain thresholds, the computer would then load syringe 10 with data representing a predetermined operating sequence. Such an operating sequence may include acceleration/deceleration patterns, flow rate data and amount of anaesthetic to administer.

The practitioner then merely sets needle 26, presses switches 18 or 22 and syringe 10 takes care of the entire injection operation. Once syringe 10 is returned to base member 34, actual volume dispensed data is transmitted to the computer and the preloaded volume data is verified with the actual volume dispensed.

The present electronic syringe is suitable for injection of biocompatible materials such as pharmaceutical (e.g. anaesthetics, insulin, etc.), vitamins, minerals, imaging dyes and the like.

It is contemplated that the materials and means described above may be substituted without departing from the spirit and scope of the invention. For example, although the above-described drive system employed an electric lead screw device, it is contemplated that pneumatic cylinders, solenoid, electromagnetic or hydraulic actuators could also be employed. Also, the electronic control means may be any suitable device including an application specific integrated circuit (ASIC) or a micro controller. It is also contemplated that a reset switch would be provided on syringe 10 to enable the practitioner to reverse the injection procedure at any time. It is further contemplated that the present electronic syringe is also suitable for aspiration of various body fluids such as bone marrow, blood, excess joint fluids and the like. In this case drive system 42 could be provided with a sliding feature and a plunger engagement means which would allow an empty ampoule to be filled with any of the above-identified fluids.

What is claimed is:

1. An electronic syringe comprising:

a pen-style elongate housing comprising a needle and electronic control means at opposite ends thereof;

an ampoule receiving first portion disposed in the housing adjacent the needle;

drive means in electrical communication with the electronic control means;

a plunger disposed between the first portion and the drive means, the drive means actuating the plunger through the first portion; and switch means located on the pen-style elongate housing between said opposite ends for actuating the drive means.

2. An electronic syringe according to claim 1, further comprising a power means coupleable to said electronic control means.

3. An electronic syringe according to claim 2, wherein said electronic control means comprises a rechargeable battery disposed within said electronic syringe, and wherein said power means comprises a battery charger detachably coupleable to said battery.

4. An electronic syringe according to claim 2, wherein said power means communicates with said electronic syringe via an umbilical cord.

5. An electronic syringe according to claims 1 or 2, further comprising a base member upon which said syringe may be mounted.

6. An electronic syringe according to claim 1, wherein said drive means comprises an electric motor.

7. An electronic syringe according to claim 6, wherein said electric motor comprises a DC stepper motor.

8. An electronic syringe according to claim 1, wherein said drive means further comprises a lead screw and a lead nut.

9. An electronic syringe according to claim 8, wherein said lead screw and said lead nut in combination provide a backlash, said backlash providing self aspiration of said ampoule.

10. An electronic device according to claim 1, said electronic control means further comprises a flow rate selector switch.

11. An electronic syringe according to claim 1, wherein said electronic control means further comprises a reset switch.

12. An electronic syringe according to claim 1, wherein said electronic control means further comprises a reverse switch.

13. A syringe according to claim 1, wherein said switch means is disposed on said housing adjacent the ampoule receiving portion.

14. An electronic syringe comprising:

a generally elongate housing comprising a needle and electronic control means at opposite ends thereof;

an ampoule receiving first portion disposed in the housing adjacent the needle;

drive means in electrical communication with the electronic control means;

a plunger disposed between the first portion and the drive means, the drive means actuating the plunger through the first portion; and switch means located on the housing between said opposite ends for actuating the drive means, wherein said electronic control means further comprises a feedback sensor mounted to said drive means which provides a signal representative of a measurement of volume injected and aspirated.

15. An electronic syringe according to claim 14, wherein said feedback sensor comprises a potentiometer strip and a wiper contact.

16. An electronic syringe according to claims 14 or 15, wherein said signal representative of said measurement is stored in said electronic control means.

17. An electronic syringe according to claim 16, wherein said electronic control means converts said signal representative of said measurement of volume injected and aspirated, to a digital signal.

18. An electronic syringe according to claim 17, wherein said electronic control means further comprises a communication means for communicating said digital signal to a processing device.

19. An electronic syringe according to claim 18, wherein said communication means comprises an asynchronous communications adapter.

20. A syringe according to claim 18, further comprising the processing device.

21. An electronic syringe according to claim 20, wherein said processing device maintains a patient database and updates said database with said digital signal representing volume injected and aspirated.

22. An electronic syringe according to claim 20 wherein said processing device comprises a computer.

23. An electronic syringe comprising:

an elongate tubular housing having a first end adapted to hold a needle and a second end disposed opposite said first end along a longitudinal axis of said elongate tubular housing;

an electrical drive unit disposed at said second end, said electrical drive unit comprising a a motor disposed along the longitudinal axis of said elongate tubular housing;

an ampoule receiving portion disposed in said housing between said first end and said electrical drive unit; and a switch disposed on said elongate tubular housing, for activating said electrical drive unit.

24. A syringe according to claim 23 wherein said electrical drive unit includes an electrical control unit disposed on said longitudinal axis and in electrical communication with said switch and said motor.

25. A syringe according to claim 23 wherein said switch comprises a first on/off finger pressure switch disposed adjacent said first end.

26. A syringe according to claim 25, wherein said first switch is activated by finger pressure applied in a direction toward said longitudinal axis.

27. A syringe according to claim 25, further comprising another on/off finger pressure switch spaced apart from said first switch in a direction toward said second end.

28. A syringe according to claim 23 wherein said electrical drive unit comprises a battery compartment disposed adjacent said second end, an electrical control unit disposed adjacent said battery compartment, and a motor disposed between said electrical control unit and ampoule receiving portion.

29. A syringe according to claim 23, wherein said switch is disposed on said housing adjacent the ampoule receiving portion.

30. An electronic syringe according to claim 23, wherein said electrical drive unit includes a battery compartment disposed along the longitudinal axis of said tubular housing.

31. An electronic syringe according to claim 23, wherein said electrical drive unit includes an electrical cable disposed along the longitudinal axis of said tubular housing.

* * * * *